(12) United States Patent
Jin et al.

(10) Patent No.: US 7,160,941 B2
(45) Date of Patent: *Jan. 9, 2007

(54) DENTAL COMPOSITE MATERIALS AND METHOD OF MANUFACTURE THEREOF

(75) Inventors: Shuhua Jin, Wallingford, CT (US); Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 187 days.

This patent is subject to a terminal disclaimer.

(21) Appl. No.: 10/665,391

(22) Filed: Sep. 19, 2003

(65) Prior Publication Data

US 2005/0038135 A1 Feb. 17, 2005

Related U.S. Application Data

(63) Continuation-in-part of application No. 10/452,269, filed on Jun. 2, 2003, and a continuation-in-part of application No. 10/136,031, filed on Apr. 30, 2002, now Pat. No. 6,653,365.

(60) Provisional application No. 60/338,116, filed on Nov. 8, 2001, provisional application No. 60/287,918, filed on May 1, 2001.

(51) Int. Cl.
*A61K 6/10* (2006.01)
*C08K 3/10* (2006.01)
*C08K 3/18* (2006.01)

(52) U.S. Cl. .............. 524/413; 524/417; 524/430; 524/439; 524/442; 524/443; 524/730; 523/109; 433/202.1; 433/204; 424/78.17; 424/78.31

(58) Field of Classification Search ............ 424/78.17, 424/78.31; 433/202.1, 204, 109; 523/109; 524/413, 417, 430, 439, 442, 443, 730
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee et al. | |
| 3,755,420 A | 8/1973 | Stoffey et al. | |
| 3,926,906 A | 12/1975 | Lee, II et al. | |
| 4,306,913 A | 12/1981 | Mabie et al. | |
| 4,544,359 A | 10/1985 | Waknine | |
| 4,547,531 A | 10/1985 | Waknine | |
| 4,764,497 A | 8/1988 | Yuasa et al. | |
| 5,276,068 A | 1/1994 | Waknine | |
| 5,444,104 A | 8/1995 | Waknine | |
| 5,484,867 A * | 1/1996 | Lichtenhan et al. | 528/9 |
| 5,856,373 A | 1/1999 | Kaisaki et al. | 522/25 |
| 5,876,210 A | 3/1999 | Klee et al. | |
| 5,936,006 A | 8/1999 | Rheinberger et al. | |
| 5,969,000 A | 10/1999 | Yang et al. | |
| 6,013,694 A | 1/2000 | Jia et al. | |
| 6,084,004 A | 7/2000 | Weinmann et al. | 522/25 |
| 6,187,833 B1 | 2/2001 | Oxman et al. | 522/15 |
| 6,187,836 B1 | 2/2001 | Oxman et al. | 522/148 |
| 6,306,926 B1 | 10/2001 | Bretscher et al. | 523/116 |
| 6,362,251 B1 | 3/2002 | Alkemper et al. | |
| 6,387,981 B1 | 5/2002 | Zhang et al. | |
| 6,417,246 B1 | 7/2002 | Jia et al. | |
| 6,572,693 B1 | 6/2003 | Wu et al. | |
| 6,653,365 B1 * | 11/2003 | Jia | 523/109 |
| 2002/0198282 A1 | 12/2002 | Jia | 523/115 |

OTHER PUBLICATIONS

Lichtenhan, Joseph D., "Polyhedral Oligomeric Silsesquioxanes: Building Blocks for Silsesquioxnae-Based Polymers and Hybrid Materials", Comments Inorg. Chem. (Mar. 1995), vol. 17, No. 2, pp. 115-130.

Lichtenhan, Joseph D., et al, "Linear Hybrid Polymer Building Blocks: Methacrylate-Functionalized Polyhedral Oligomeric Silsesquioxane Monomers and Polymers", Macromolecules (Nov. 1995) vol. 28, pp. 8435-8437.

NASA High-Performance POSS-Modified Polymeric Composites, NASA Tech Briefs, Feb. 2001, p. 52.

Feher, Frank J., et al, "Silsesquioxanes As Models For Silica Surfaces", American Chemical Society, (Mar. 1989), vol. 111, pp. 1741-1748.

* cited by examiner

*Primary Examiner*—Kriellion Sanders
(74) *Attorney, Agent, or Firm*—Cantor Colburn LLP

(57) ABSTRACT

A dental composite material that comprises a polyhedral oligomeric silsesquioxane is disclosed. The dental composite material is useful for a variety of dental materials, treatments, and restorative functions including crown and bridge materials, fillings, adhesives, sealants, luting agents or cements, denture base materials, orthodontic materials and sealants, and other dental restorative materials.

30 Claims, No Drawings

DENTAL COMPOSITE MATERIALS AND METHOD OF MANUFACTURE THEREOF

CROSS-REFERENCE TO RELATED APPLICATIONS

This application is a continuation-in-part of U.S. Pat. No. 6,653,365 (application Ser. No. 10/136,031 filed Apr. 30, 2002), which claims the benefit of U.S. Provisional Patent Application Ser. No. 60/287,918 filed May 1, 2001 and U.S. Provisional Patent Application No. 60/338,116, filed Nov. 8, 2001. This application further is a continuation-in-part of U.S. patent application Ser. No. 10/452,269 filed Jun. 2, 2003. All of the foregoing being fully incorporated herein by reference.

BACKGROUND OF THE INVENTION

This invention relates to composite materials and to the methods for the manufacture of such composite materials for restorative dentistry, and more particularly to composites which are useful as crown and bridge materials, either with or without an alloy substrate, as reconstructive materials, restorative materials, filling materials, inlays, onlays, laminate veneers, dental adhesives, cements, sealants and the like.

In recent years, materials used for dental restorations have comprised principally acrylate or methacrylate resins. Typical acrylic resinous materials are disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al. and U.S. Pat. No. 3,926,906 to Lee et al. Acrylic resinous materials, however, exhibit high coefficients of thermal expansion relative to the coefficient of thermal expansion for the tooth structure, and therefore these substances by themselves proved to be less than satisfactory. The disparity in thermal expansion, coupled with high shrinkage upon polymerization, results in poor marginal adaptability, and ultimately leads to secondary decay. Furthermore, the wear and abrasion characteristics and the overall physical, mechanical, and optical properties of these unfilled acrylic resinous materials were quite poor. Composite dental restorative materials containing acrylate or methacrylate resins and fillers were thus developed, the fillers generally comprising inorganic materials based on silica, silicate glass, or quartz. Particularly suitable improved inorganic filler materials include those disclosed in commonly assigned U.S. Pat. No. 4,547,531 to Waknine, and U.S. Pat. No. 4,544,359 to Waknine. These filled compositions are useful for a variety of dental treatments and restorative functions including crown and bridge materials, fillings, adhesives, sealants, luting agents or cements, denture base materials, orthodontic materials and sealants, and other dental restorative materials. Despite their suitability for their intended purposes, however, there nonetheless remains a need in the art for dental resin materials with even more advantageous physical properties.

SUMMARY OF THE INVENTION

An improved dental composite material comprises a polymerizable, ethylenically unsaturated resin composition; a filler composition comprising a modified polyhedral oligomeric silsesquioxane filler; and a curing system. In another embodiment, a dental composite material comprises a modified polyhedral oligomeric silsesquioxane resin; and a curing system. These dental composite materials are useful in a variety of dental materials, treatments, and restorative functions, including crown and bridge materials, fillings, adhesives, sealants, luting agents or cements, denture base materials, orthodontic materials and sealants, and other dental restorative materials.

DETAILED DESCRIPTION OF THE PREFERRED EMBODIMENTS

A new dental restorative composition comprises a polymerizable resin composition and a polyhedral oligomeric silsesquioxane (POSS) filler. POSS-filled resins typically exhibit lower mass densities and greater stiffness, and are capable of withstanding higher temperatures, as well as higher levels of ionizing radiation. In addition, POSS-filled resins are capable of wetting fibers to desirably high degrees. The use of POSS with dental resin materials, particularly the acrylate/methacrylate resins, minimizes polymerization shrinkage and increases material toughness. The nanoscale dimensionality of the POSS fillers also allows for better aesthetic properties, including easier polishability and improved transparency.

Resin compositions suitable for use with dental restorations are well known in the art, and generally comprise ethylenically unsaturated groups that are polymerizable. Especially useful are the polymerizable acrylate or methacrylate resins such as those disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al., U.S. Pat. No. 3,926,906 to Lee et aL, and commonly assigned U.S. Pat. Nos. 5,276,068 and No. 5,444,104 to Waknine, all of which are incorporated herein by reference. Other suitable resin materials include, but are not limited to, various polyurethane dimethacrylates (PUDMA), diurethane dimethacrylates (DUDMA), and other monomers and oligomers known in the art. A useflul monomer disclosed in U.S. Pat. No. 5,276,068 and 5,444,104 to Waknine is polycarbonate dimethacrylate (PCDMA) which is the condensation product of two parts of a hydroxyalkyl-methacrylate and 1 part of a bis(chloroformate). Another advantageous resin having lower water sorption characteristics is an ethoxylated bisphenol A dimethacrylate (EBPDMA) as disclosed in U.S. Pat. No. 6,013,694. An especially important methacrylate resin is the condensation product of bisphenol A and glycidyl methacrylate, 2,2'-bis[4-(3-methacryloxy-2-hydroxy propoxy)-phenyl]-propane (hereinafter abbreviated "Bis-GMA"). Included within the scope of the resin compositions herein are the resin compositions suitable for use with glass ionomer cements, including polycarboxylic acids such as homo- and copolymers of acrylic acid and/or itaconic acid.

In addition to the aforementioned resins and oligomers, the resin compositions can further include a diluent acrylate or methacrylate monomer to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; and diol dimethacrylates such as 1,4-butanedioldimethacrylate, dodecanedioldimethacryalte, or 1,6-hexanedioldimethacrylate (HDDMA). Tri(ethylene glycol) dimethacrylate (TEGDMA) is particularly preferred.

The more viscous polymerizable ethylenically unsaturated resins, i.e., PUDMA, Bis-GMA, and the like are generally present in an amount greater than or equal to about 30, preferably greater than or equal to about 50 wt % of the total composition. It is generally desirable to have the polymerizable ethylenically unsaturated resins less than or equal to about 99, preferably less than or equal to about 90, more preferably less than or equal to about 80 wt % of the total composition. Diluent monomers, when present, are incorporated into the resin composition in an amount from about 1 to about 70 wt % of the total resin composition.

In one embodiment, the ethylenically unsaturated resin composition comprises both at least one ethylenically unsaturated group and at least one epoxide group in the same molecule.

In addition to the above monomers and oligomers, the resin compositions also include a curing system, which typically include polymerization initiators and polymerization accelerators; ultraviolet light absorbers; antioxidants; and other additives known in the art.

Suitable polymerization initiators are those conventional initiators known in the art. For example, visible light curable compositions employ light-sensitive compounds, including but not being limited to benzil, benzoin, benzoin methyl ether, DL-camphorquinone (CQ), and benzil diketones. Either UV-activated cure or visible light-activated cure (approximately 230 to 750 nm) is acceptable. The amount of photoinitiator is selected according to the curing rate desired. A minimal catalytically effective amount is generally about 0.01 wt % of the polymerizable resin composition, and will lead to a slower cure. Faster rates of cure are achieved with amounts of catalyst in the range from greater than about 0.01 percent to about 5 wt % of the resin composition.

Alternatively, the composition may be formulated as a self-curing system. Self-curing compositions will generally contain free radical polymerization initiators such as, for example, a peroxide in amounts ranging from about 0.01 to about 1.0 wt % of the resin composition. Particularly suitable free radical initiators are lauryl peroxide, tributyl hydroperoxide and, more particularly benzoyl peroxide.

Polymerization accelerators suitable for use are the various organic tertiary amines well known in the art. In visible light curable compositions, the tertiary amines are generally acrylate derivatives such as dimethylaminoethyl methacrylate and, particularly, diethylaminoethyl methacrylate (DE-AEMA) in amounts ranging from about 0.05 to about 0.5 wt % of the resin composition. In the self-curing compositions, the tertiary amines are generally aromatic tertiary amines, preferably tertiary aromatic amines such as ethyl 4-(dimethylamino)benzoate (commonly known as "EDMAB"), 2-[4-(dimethylamino)phenyl] ethanol, N,N-dimethyl-p-toluidine (commonly abbreviated "DMPT"), bis(hydroxyethyl)-p-toluidine, and triethanolamine. Such accelerators are generally present in the range from about 0.5 to about 4.0 wt % of the resin composition.

It is furthermore preferred to employ an ultraviolet absorber in amounts ranging from about 0.05 to about 5.0 wt % of the total composition. Such UV absorbers are particularly desirable in the visible light curable compositions in order to avoid discoloration of the resin from any incident ultraviolet light. Suitable UV absorbers are the various benzophenones, particularly UV-5411 available from American Cyanamid Company.

The dental composition further comprises at least one polyhedral oligomeric silsesquioxane (POSS) of the generic formula $(RSiO_{1.5})_n$, wherein R is a hydrocarbon and n is 6, 8, 10, 12, or higher. These molecules have rigid, thermally stable silicon-oxygen frameworks with an oxygen to silicon ratio of 1.5, and covalently-bound hydrocarbon groups that provide an organic outer layer comprising, for example, phenyl, isooctyl, cyclohexyl, cyclopentyl, isobutyl, or other groups. Such silsesquioxanes include, for example, dodecaphenyl-POSS, octaisooctyl-POSS, octacyclohexyl-POSS, octacyclopentyl-POSS, octaisobutyl-POSS and the like. POSS typically have surface areas greater than 400 square meters per gram ($m^2/gm$).

Functionalized POSS (also known as "POSS monomers") are particularly preferred, wherein one, two, or more of the covalently bound organic groups are reactive with at least one component of the resin composition. In some cases, it is possible to have all of the covalently bound organic groups be reactive groups. POSS monomers may be prepared, for example, by corner-capping an incompletely condensed POSS containing trisilanol groups with a substituted trichlorosilane. For example, the trisilanol functionality of $R_7T_4D_3(OH)_3$ (wherein R is a hydrocarbon group) can be reacted with $Cl_3Si-Y$ to produce the fully condensed POSS monomer $R_7T_8Y$.

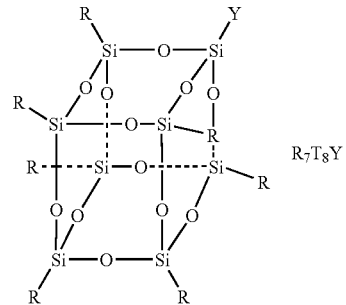

$R_7T_8Y$

Through variation of the Y group on the silane, a variety of functional groups can be placed off the corner of the POSS framework, including but not limited to halide, alcohol, amine, isocyanate, acid, acid chloride, silanols, silane, acrylate, methacrylate, olefin, and epoxide.

Further examples of POSS monomers include those of the general formula $R_{n-m}T_nY_m$ wherein R is a hydrocarbon; n is 6, 8, 10, 12 or higher; m is 1 to n; T is $SiO_{1.5}$, and Y is an organic group comprising a functional group, wherein the functional group includes, for example, halide, alcohol, amine, isocyanate, acid, acid chloride, silanols, silane, acrylate, methacrylate, olefin, and epoxide. A preferred POSS monomer has an n of 8; m of 1, 2, 3, 4, 5, 6, 7, or 8; R of $C_1-C_{24}$ straight, branched, or cyclic alkyl, $C_1-C_{24}$ aromatic, alkylaryl, or arylakyl, wherein the alkyl or aromatic is optionally substituted with $C_1-C_6$ alkyl, halo, $C_1-C_6$ alkoxy, $C_1-C_6$ perhaloalkyl, and the like.

Another preferred POSS monomer includes those of the general formula $R_7T_4D_3(OY)_3$

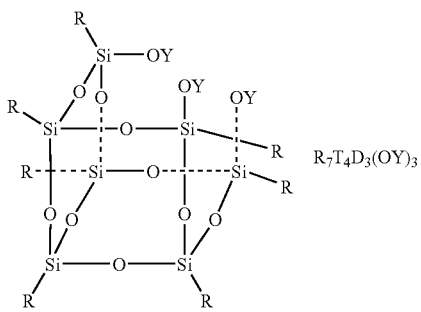 $R_7T_4D_3(OY)_3$ wherein R and Y are as defined previously for the $R_7T_8Y$ POSS monomer; T is $SiO_{1.5}$, and D is SiO.

Preferred functional groups of the Y group are acrylate (—X—OC(O)CH=$CH_2$) and methacrylate (—X—OC(O)CH($CH_3$)=$CH_2$) groups, wherein X is a divalent linking group having 1 to about 36 carbons, such as methylene, ethylene, propylene, isopropylene, butylene, isobutylene, phenylene, and the like. X may also be substituted with functional groups such as ether (e.g., —$CH_2CH_2OCH_2CH_2$—), as long as such functional groups do not interfere with formation or use of the POSS. X is preferably propylene, isobutylene, or —$OSi(CH_3)_2CH_2CH_2CH_2$—. One, all, or an intermediate number of the covalently bound groups may be acrylate or methacrylate groups. Such functionalized POSS are available from Gelest, Inc. (Tullytown, Pa.) and Hybrid Plastics. A methacryloxypropyl-substituted $T_8$ POSS (wherein all positions of the polyhedron are methacryloxypropyl-substituted) is available under the trade designation MA0735 from Hybrid Plastics Corp.). Another methacryloxypropyl-substituted $T_8$ POSS (wherein one position is methacryloxypropyl-substituted and the remaining positions are isobutyl-substituted) is available under the trade designation MA0702 from Hybrid Plastics Corp (Fountain Valley, Calif.).

Of course, the linking groups X are also suitable for use with other functional groups. Other POSS fillers include, for example $T_6$, $T_8$, $T_{10}$, or $T_{12}$ structures functionalized with alkoxysilanes such as diethoxymethylsilylethyl, diethoxymethylsilylpropyl, ethoxydimethylsilylethyl, ethoxydimethylsilylpropyl, triethoxysilylethyl, and the like; with styrene, such as styrenyl ($C_6H_5CH$=CH—), styryl (—$C_6H_4CH$=$CH_2$) and the like; with olefins such as allyl, —$OSi(CH_3)_2CH_2CH_2$=$CH_2$, cyclohexenylethyl, —OSi$(CH_3)_2CH$=$CH_2$ and the like; with epoxies, such as 4-propyl-1,2-epoxycyclohexyl, (2-(7-oxa-bicyclo[4.1.0]heptan-3-yl)ethylene, 3-propoxy, glycidyl, (—$CH_2CH_2CH_2OCH_2CH(O)CH_2$), —$OSi(CH_3)_2CH_2CH_2CH_2OCH_2CH(O)CH_2$, and the like; with chlorosilanes such as chlorosilylethyl, dichlorosilylethyl, trichlorosilylethyl, and the like; with amines such as aminopropyl, aminoethylaminopropyl, and the like; with alcohols and phenols such as —$OSi(CH_3)_2CH_2CH_2CH_2OC(CH_2CH_3)_2(CH_2CH_2OH)$, 4-propylene-trans-1,2-cyclohexanediol, —$CH_2CH_2CH_2OCH_2C(CH_2OH)_2(OH)$, —$OSi(CH_3)_2CH_2CH_2CH_2OC(CH_2OH)_2(CH_2CH_3)$, and the like; with phosphines such as diphenylphosphinoethyl, diphenylphosphinopropyl, and the like; with norbornenyls such as norbornenylethyl; with nitriles such as cyanoethyl, cyanopropyl, —$OSi(CH_3)_2CH_2CH_2CH_2CN$, and the like; with isocyanates such as isocyanatopropyl, —$OSi(CH_3)_2CH_2CH_2CH_2NCO$, and the like, with halides such as 3-chloropropyl, chlorobenzyl (—$C_6H_4CH_2Cl$), chlorobenzylethyl, 4-chlorophenyl, trifluoropropyl (including a $T_8$ cube with eight trifluoropropyl substitutions) and the like; and with esters, such as ethyl undecanoat-1-yl and methyl propionat-1-yl, and the like. Certain polymers such as poly(dimethylcomethylhydrido-co-methylpropyl polymers, poly(dimethylcomethylvinyl-co-methylethylsiloxy, poly(ethylnorbonenyl-co-norbonene) and poly(ethylsilsesquioxan) may also be used to functionalize POSS. Many of these substitutions are commercially available on $T_8$ POSS from Hybrid Plastics.

Without being bound by theory, it is hypothesized that the functionalization of the cubes allow for better dispersion in and reactivity with the matrix resin, which reduces moisture uptake, as well as volumetric shrinkage. Bonding of the $T_8$ cubes with the matrix resin may be achieved by co-polymerization with the resin monomers or oligomers in the presence of a cure system, for example by treatment with radiation such as UV light.

Alternatively, the POSS monomer comprising at least one Y group having reactive functionality may further be synthetically modified to form a "modified POSS". A "modified polyhedral oligomeric silsesquioxane" ("modified POSS") is the reaction product of a POSS monomer comprising at least one Y group having reactive functionality and an organic compound comprising two or more reactive functionalities at least on of which reacts with Y functionality. For example, a POSS monomer according to the general formula $R_7T_8Y$ may be converted to a modified POSS of formula $R_7T_8J$ by the reaction of the reactive functionality of the Y group with an organic compound (J*) which comprises two or more reactive functionalities to result in a J group, which is the reaction product of Y and J*. J preferably comprises one or more functional groups that is reactive with at least one component of the resin composition. Reactive groups suitable for the functional group of J include, for example, halide, alcohol, amine, isocyanate, acid, acid chloride, silanols, silane, acrylate, methacrylate, olefin, and epoxide. The particular methods by which the functional group of Y can be synthetically modified to result in J groups can readily be determined by one of ordinary skill in the art without undue experimentation. An example of preparing a modified POSS includes reacting a POSS monomer according to the formula $R_7T_8Y$ wherein the functional group on Y is an epoxide with one equivalent of J* which is a (meth)acrylic acid in the presence of an appropriate catalyst and solvent, and optional heating. The resulting modified POSS would be the reaction product $R_7T_8J$ wherein the J group comprises (meth)acrylate functionality and the secondary hydroxy from the ring opening reaction.

Alternatively, depending upon the POSS monomer starting material, the J* compound, the ratios of the two starting materials, and reaction conditions, the modified POSS may be in the form of a monomer, oligomer, polymer, or a mixture of reaction products including at least one of the foregoing compounds. For instance, a POSS monomer according to the general formula $R_{n-m}T_nY_m$ wherein m is 2 or more, may further be synthetically modified to form a modified POSS of formula $R_{n-m}T_nY_{m-p}J_p$ by the reaction with one or more equivalents of organic compound (J*). The p may be an integer from 1 to m, wherein m and n have been defined above. Adjusting the molar ratios of Y to J* may result in a mixture of reaction products comprising partial or complete conversion of the Y groups to J in addition to further polymerized products.

In yet another example, where the POSS monomer comprises more than one Y group, as in the general formula $R_7T_4D_3(OY)_3$, adjusting the molar ratios of Y functional groups to the reactive organic group (J*) results in partial to complete conversion of the Y to J groups. For example, one equivalent of $R_7T_4D_3(OY)_3$, wherein the functional group of Y is an epoxide, is reacted with one equivalent of J* which is (meth)acrylic acid, or a methacrylate terminated carboxylic acid, wherein the ratio of epoxide to (meth)acrylic acid or (meth)acrylate terminated carboxylic acid is 3 to 1, to form a ring opened product. The resulting modified POSS would include the reaction product $R_7T_4D_3(OY)_2(OJ)$ wherein the Y group comprises epoxy functionality and the J group comprises (meth)acrylate functionality. Again, the resulting modified POSS may also include other reaction products, such as the product resulting from the reaction of the secondary hydroxyl of the ring-opened epoxide with another epoxy ring of a Y group to form a polymerized product. By controlling the reaction conditions, such as ratio of J* to Y groups, the reaction temperature and time, and the amount of catalyst, the reaction product may comprise a variety of one or more compounds, including modified POSS monomer, oligomer, and/or polymers.

The ratio of Y functional groups to J* functional groups in a reaction mixture may be selected to control the outcome of the desired product. Exemplary ratios of Y functional groups to J* may be about 10:1 to about 1:10, preferably about 5:1 to about 1:5; more preferably about 2:1 to about 1:2, and even more preferably about 1:1.

In one embodiment, the POSS monomer used to prepare the modified POSS comprises a Y group having a functional group which includes epoxy, hydroxy, phenol, and the like. Within this embodiment, the J* compounds comprise at least one (meth)acrylate functionality and further functional groups that may react with the functional groups of Y, including epoxy, carboxylic acid, hydroxy, phenol, and the like.

When the functional group of Y is epoxy, the preferred organic compound J* used to prepare the modified POSS is (meth)acrylate terminated carboxylic acid or a hydroxy (meth)acrylate. Hydroxy(meth)acrylate as used herein includes compounds of the general formula

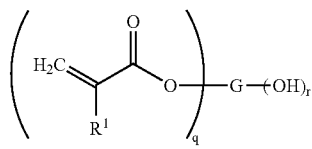

wherein q and r are independently integers from 1 to 6; G is a substituted or unsubstituted $C_1$–$C_{33}$ alkyl, substituted or unsubstituted aryl group, or ($C_1$–$C_6$) alkyl-oxy-($C_1$–$C_6$) alkyl; and $R^1$ is hydrogen or methyl. Suitable substitution on the G moiety includes, for example, linear or branched, saturated or unsaturated $C_1$–$C_{12}$ alkyl; $C_1$–$C_{12}$ alkoxy; cyclic $C_3$–$C_7$ alkyl; halogens; ester groups; ether groups; amide groups; aryl; and the like. A preferred hydroxy (meth)acrylate is where q is 1 and r is 1.

Non-limiting examples of suitable hydroxy (meth)acrylates include caprolactone 2-(methacryloyloxy) ethyl ester (CLMA); 2-hydroxyethyl acrylate; 2-hydroxyethyl methacrylate (HEMA); 3-hydroxypropyl (meth)acrylate; 4-hydroxybutyl (meth)acrylate; polyethylene glycol mono(meth)acrylate; glycerol di(meth)acrylate; trimethylolpropane di(meth)acrylate; pentaerythritol tri(meth)acrylate; and the (meth)acrylate of phenyl glycidyl ether. Blends of the aforementioned hydroxy (meth)acrylates can also be used to form the polymerizable dental resin. The most preferred hydroxy acrylate or hydroxy methacrylate is CLMA and HEMA.

In another embodiment, J* is a molecule comprising at least one epoxy group and at least one (meth)acrylate group. Exemplary J* groups of this type include glycidyl (meth) acrylate; 2-((oxiran-2-yl)methoxy)ethyl acrylate; 3-((oxiran-2-yl)methoxy)propyl acrylate; and the like. Within this embodiment, the Y functional group of the POSS monomer is preferably hydroxy, phenol, or carboxyl.

The catalyst used in the epoxide ring opening reaction to form the modified POSS may be selected from those used in conventional cationic, anionic or coordination ring-opening polymerization. Preferred catalysts are metal organic catalysts comprising tin or titanium. Suitable non-limiting examples of tin-containing catalysts are dibutyltin dilaurate, dibutyltin maleate, dibutyltin diacetate, dioctyltin maleate, dibutyltin phthalate, stannous octoate, stannous naphthenate, stannous stearate, stannous 2-ethyl hexanoate, dibutyltin diacetylacetonate, dibutyltin oxide, and combinations comprising at least one of the foregoing tin based catalysts. Suitable non-limiting examples of titanium-based catalysts are tetrabutyl titanate, tetrapropyl titanate, tetraisopropyl titanate, triethanolamine titanate, titanium tetraacetylacetonate, and combinations comprising at least one of the foregoing titanium based catalysts. The preferred catalysts are stannous octoate or stannous 2-ethyl hexanoate.

It is generally desirable to use the catalyst in an amount of about 0.10 to about 10 mole percent (mole %) based on the total moles of the reactant mixture. Within this range it is generally desirable to utilize the catalyst in an amount of greater than or equal to about one, preferably greater than or equal to about 2, and most preferably greater than or equal to about 3 mole % based on the total moles of the reactants. Within this range, it is generally desirable to utilize the catalyst in an amount of less than or equal to about 8, and preferably less than or equal to about 7 mole % based on the total moles of the reactants.

In a preferred embodiment, the modified POSS comprises (meth)acrylate functionality or a combination of epoxy and (meth)acrylate functionality.

Advantageously, the POSS monomers that have been synthetically modified, as described above, to result in a modified POSS may be used either as a filler or, alternatively, as a resin component of a dental composite matrix rather than as a filler. These synthetically modified POSS monomers used as polymerizable resin components are described herein as modified POSS resins. Preferably the modified POSS resin is a (meth)acrylate and/or epoxy resin, which comprises a POSS structure. The modified POSS compounds comprising (meth)acrylate and/or epoxy functionality and their description of preparation as described above may be used as the modified POSS resin. The modified POSS resin exhibits desirable properties for use a dental matrix component as it tends to be in liquid form, is more hydrophobic due to the presence of the silicon molecules, and has a higher molecular weight thereby providing lower water sorption and lower polymerization shrinkage of the resulting dental restorative composite.

When used as a resin in a dental restorative composition, the modified POSS resin is generally present in an amount greater than or equal to about 10, preferably greater than or equal to about 30 wt % of the total composition. It is generally desirable to have the modified POSS resin in an amount of less than or equal to about 99, preferably less than or equal to about 90, more preferably less than or equal to about 80 wt % of the total composition.

The modified POSS resin may be used in combination with polymerizable ethylenically unsaturated resins as described herein. When used in combination with polymerizable ethylenically unsaturated resins, the amount of modified POSS resin may be present in an amount greater than or equal to about 1, preferably greater than or equal to about 20, and more preferably greater than or equal to about 40 wt % based on the total of modified POSS resin and polymerizable ethylenically unsaturated resin. It is generally desirable to have the modified POSS resin in an amount of less than or equal to about 99, preferably less than or equal to about 80, and more preferably less than or equal to about 60 wt % based on the total of modified POSS resin and polymerizable ethylenically unsaturated resin.

Diluent monomers, when present with the modified POSS resin, are incorporated into the composition in an amount from about 1 to about 70 wt % of the total composition.

Also contemplated herein is a filler combination comprising a POSS filler and modified POSS filler.

In addition to the POSS-based filler, the filler composition may further comprise one or more of the inorganic fillers currently used in dental restorative materials. Preferred additional fillers include those that are capable of being covalently bonded to the resin matrix itself or to a coupling agent that is covalently bonded to both. Examples of suitable filling materials include but are not limited to, silica, quartz, strontium silicate, strontium borosilicate, lithium silicate, lithium alumina silicate, amorphous silica, ammoniated or deammoniated calcium phosphate, tricalcium phosphate alumina, zirconia, tin oxide, and titania. Some of the aforementioned inorganic filling materials and methods of preparation thereof are disclosed in U.S. Pat. Nos. 4,544,359 and No. 4,547,531, pertinent portions of which are incorporated herein by reference. Suitable high refractive index filler materials such as high refractive index silica glass fillers and calcium silicate based fillers such as apatites, hydroxyapatites or modified hydroxyapatite compositions may also be used. Alternatively, inert, non-toxic radiopaque materials such as bismuth oxide ($Bi_2O_3$), barium sulfate, and bismuth subcarbonate may be used. Suitable fillers have a particle size in the range from about 0.1 to about 5.0 microns, and may further comprise unbound silicate colloids of about 0.001 to about 0.07 microns. These additional fillers may also be silanized.

The amount of total filler composition in the dental composite can vary widely, being in the range from about 1 to about 90 wt % of the total composition. The amount used is determined by the requirements of the particular application. Thus, for example, crown and bridge materials generally comprise from about 60 to about 90 wt % filler; luting cements comprise from about 20 to about 80 wt % filler; sealants generally comprise from about 1 to about 20 wt % filler; adhesives generally comprise from about 1 to about 30 wt % filler; and restorative materials comprise from about 50 to about 90 wt % filler, with the remainder in all cases being the resin composition and curing system.

The amount of POSS in the filler composition relative to other filler may also vary widely, depending on the requirements of the particular application. The POSS may accordingly comprise from less than about 1 to 100 wt % of the total filler composition, preferably from about 1 to about 100 wt % of the total filler composition for sealers and adhesives, and from about 2 to about 30 wt % of the total filler composition for crown and bridge materials and dental restorative materials.

In a preferred embodiment, in one manner of proceeding the polymerizable resin composition (including any desired diluent monomers), the POSS filler, and any additional fillers are mixed. The curing system is added to the mixture, which is again stirred and stored or used, as appropriate. The cure may be initiated through the use of UV light or by raising the temperature of the mixture. The dental restorative resin thus obtained is then placed in the tooth to be repaired after it is appropriately prepared. Methods for use of the above-described compositions are well known in the art. The invention is further illustrated by the following non-limiting examples.

EXAMPLES

Example 1

Water Sorption and Solubility

A resin matrix was prepared wherein 30 grams of EBP-DMA, 50 grams of PUDMA and 20 grams of HDDMA were mixed in a beaker with a magnetic stirring bar. Photoinitiator (0.1 grams of camphorquinone, 0.3 grams of EDMAB and 0.2 grams of Lucirin™ TPO) was added into the resin mix and allowed to dissolve completely.

This photocurable resin composition was then used as a resin matrix and three more compositions were generated by adding (1) 30% wt POSS (methacryloxypropyl substituted polycyclopentyl $T_8$ silsesquioxane from Gelest, Inc, available under the trade designation SST-H8C51); (2) 30 wt % silane treated OX-50 silica (Degussa Corp.) and (3) 20% T-530, a surface treated silica (Cabot, Inc.) (because of the high surface area of T-530, only 20 wt. % can be incorporated to obtain a workable composite). Three sample discs (1 mm thick, 15 mm diameter) were prepared for each composition and cured in a light chamber (Cure-Lite Plus, Jeneric/Pentron, Inc.) for two minutes. Water sorption and water solubility tests were conducted according to ISO 4049. Test results are shown in Table 1. (All water sorption and solubility data has been rounded to one digit decimal place.)

TABLE 1

| Composition | Water sorption (S.D.)**, micrograms/cubic mm | Solubility (S.D.), micrograms/cubic mm |
|---|---|---|
| Resin only* | 15.1 (0.7) | 7.7 (0.4) |
| Resin with 30% POSS | 12.5 (0.1) | 1.0 (0.1) |
| Resin with 30% OX-50* | 14.2 (0.1) | 3.2 (0.2) |
| Resin with 20% T-530* | 13.6 (0.1) | 7.1 (0.2) |

*Comparative example
**(S.D.) = Standard deviation

The water sorption and solubility test results show clearly that the addition of POSS into dental methacrylate resin decreases the water sorption and solubility of the polymer dramatically. The POSS, when used as filler, performs much better than conventional fillers such as fumed silica in reducing the water sorption and solubility for a dental polymer.

Example 2

Polymerization Shrinkage

The following paste/putty-like composite formulations were prepared for the volume shrinkage measurements. Measurements were performed using a computer-controlled mercury dilatometer developed by the National Institutes of Science and Technology (NIST)/American Dental Association Health Foundation. The samples tested were as follows:

Group 1: The basic resin composition as in Example 1 comprising 60 wt % of POSS particles;

Group 2: The basic resin composition as in Example 1 comprising 60 wt % of silane treated OX-50;

Group 3: The basic resin composition as in Example 1 comprising 15 wt % of the above POSS and 45 wt % silane treated OX-50;

Group 4: The basic resin composition as in Example 1 comprising 15 wt % of the above POSS, 15 wt % silane treated OX-50 and 50 wt % of a silane surface treated barium borosilicate glass filler with average particle size of 0.7 micrometers.

Group 5: The basic resin composition as in Example 1 comprising 0 wt % POSS, 15 wt % silane treated OX-50 and 65 wt % of the silane treated 0.7 micrometer barium borosilicate glass filler.

Each testing material was subjected to two testing runs with the dilatometer. A total of 90 minutes was needed for each run. Initial light curing time was 60 seconds. A second-time light cure of 30 seconds was followed 60 minutes after the initial light curing of the test material according to the test procedure. The average test result for each material is shown in Table 2 below.

TABLE 2

| Sample Groups | Polymerization Volume Shrinkage (%) |
| --- | --- |
| Group 1 | 2.39 |
| Group 2* | 3.44 |
| Group 3 | 2.83 |
| Group 4 | 2.05 |
| Group 5* | 2.58 |

*Comparative Example

As may be seen from the above data, the polymerization shrinkage test data surprisingly suggests that the addition of a POSS into a dental methacrylate resin composition decreases the volume shrinkage of the composition upon polymerization when compared with traditional colloidal silica fillers.

Example 3

Polymerization Shrinkage Test

In this example, a dental resin comprising polymerizable ethylenically unsaturated methacrylates (FLOW-IT® ALC A2, from Pentron Corp.) was combined with silanated OX-50, a colloidal silica as the control sample, or with a combination of colloidal silica and methacryl isobutyl-POSS (MA0702, from Hybrid Plastics Corp.). The volume shrinkage on both samples was measured after curing.

TABLE 3

| Components | Weight Percent | Volume Shrinkage (%) |
| --- | --- | --- |
| FLOW-IT ® ALC A2 | 66.66 | 2.4 |
| POSS MA0702 | 16.65 | |
| Silanated OX-50 | 16.65 | |
| FLOW-IT ® ALC A2 | 66.66 | 3.0 |
| Silanated OX-50 | 33.33 | |

The above results show that replacement of a portion of the colloidal silica with the POSS helps reduce the volume shrinkage upon curing.

Example 4

Water Sorption and Solubility

In this example, a dental sealant (PROTECT-IT, from Pentron Corporation) was mixed with 10 wt % of methacryl-POSS Cage Mixture (MA0735, from Hybrid Plastics Corp.) or 10 wt % methacrylisobutyl-POSS, (MA0702 from Hybrid Plastics Corp.). PROTECT-IT Sealant without any POSS filler was used as a control sample. Results are shown in Table 4:

TABLE 4

| Components | Water Sorption (micrograms/mm$^3$/ week) (S.D.) | Water Solubility (micrograms/mm$^3$/ week) (S.D.) |
| --- | --- | --- |
| PROTECT-IT with 10% MA0735 | 20.4 (0.7) | 7.1 (0.5) |
| PROTECT-IT with 10% MA0702 | 25.4 (0.5) | 6.9 (0.4) |
| PROTECT-IT Sealant* | 29.3 (0.8) | 7.3 (0.4) |

*Control

The data shown in Table 4 below shows that water or sorption and water solubility are significantly reduced when POSS is used as a filler.

Example 5

Dentin Bonding

In this example, dentin surfaces were first etched with 37% $H_3PO_4$ etching gel for 20 seconds and then water rinsed. An adhesive formulation (BOND-1™, Pentron Corporation) with or without POSS (either methacryl-POSS MA0735 or methacryl isobutyl-POSS, MA0702) was then applied onto the dentin surfaces. The solvent in the adhesive was air-dried and the adhesive was light cured for 10 seconds. SCULPT-IT™ composite (Pentron, Corporation.) was used on top of the adhesive to form a small cylinder of 3.5 mm diameter and about 3 mm height. Samples were stored in water at 37° C. for 24 hours before the de-bonding test. Six samples of dentin bonding samples were tested for each material. The results were averaged and are shown in Table 5 below wherein it can be seen that in general the bond strength is greater for resins containing POSS fillers.

TABLE 5

| Components | Dentin Bonding Strength MPa (S.D.)** |
|---|---|
| BOND-1* (Control) | 20.2 (2.2) |
| BOND-1 with 4% MA 0735 | 23.7 (2.5) |
| BOND-1 with 2% MA 0735 | 22.9 (4.1) |
| BOND-1 with 4% MA 0702 | 19.5 (3.1) |

*Control
*(S.D.) = Standard deviation

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A dental restorative composition comprising:
   a polymerizable, ethylenically unsaturated dental restorative resin composition;
   a filler composition comprising a modified polyhedral oligomeric silsesquioxane filler; and
   a curing system.

2. The composition of claim 1, wherein the resin composition comprises an acrylate or methacrylate resin.

3. The composition of claim 2, wherein the resin composition further comprises 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, butanedioldimethacrylate, dodecanedioldimethacrylate, 1,6-hexanedioldimethacrylate, or a mixture comprising at least one of the foregoing methacrylate monomers.

4. The composition of claim 1, wherein the resin composition comprises polyurethane dimethacrylate, diurethane dimethacrylate, polycarbonate dimethacrylate, ethoxylated bisphenol A dimethacrylate, 2,2'-bis [4-(3-methacryloxy-2-hydroxy propoxy)-phenyl]-propane, or a mixture comprising at least one of the foregoing resins.

5. The composition of claim 1, wherein the modified polyhedral oligomeric silsesquioxane filler comprises at least one functional group reactive with the resin composition.

6. The composition of claim 5, wherein the reactive group comprises halide, alcohol, amine, isocyanate, acid, acid chloride, silanol, silane, acryl, methacryl, olefin, epoxy, or a mixture comprising at least one of the foregoing reactive groups.

7. The composition of claim 5, wherein the reactive group comprises an acryl or methacryl.

8. The composition of claim 5, wherein the reactive group comprises an alkoxysilane, a styrene, an olefin, an epoxy, a chlorosilane, an amine, an alcohol, a phenol, a phosphine, a norbornenyls, a nitrile, an isocyanate, a halide, an ester, or a mixture comprising at least one of the foregoing reactive groups.

9. The composition of claim 1, wherein the modified polyhedral oligomeric silsesquioxane filler is the reaction product of
   a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; and Y is an organic group comprising an epoxy functional group; or a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising an epoxy functional group; and a (meth)acrylic acid, or a hydroxy (meth)acrylate of the formula

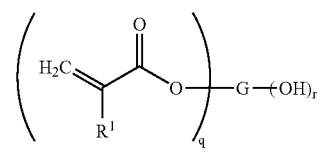

wherein q and r are independently integers from 1 to 6; G is a substituted or unsubstituted $C_1$–$C_{33}$ alkyl, substituted or unsubstituted aryl group, or ($C_1$–$C_6$) alkyl-oxy-($C_1$–$C_6$) alkyl; and $R^1$ is hydrogen or methyl, wherein the substitution is linear or branched, saturated or unsaturated $C_1$–$C_{12}$ alkyl; $C_1$–$C_{12}$ alkoxy; cyclic $C_3$–$C_7$ alkyl; halogens; ester groups; ether groups; amide groups; aryl; or a combination comprising at least one of the foregoing substitutions.

10. The composition of claim 1, wherein the modified polyhedral oligomeric silsesquioxane filler is the reaction product of
    a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; and Y is an organic group comprising a hydroxy functional group, a phenol functional group, or a carboxyl functional group; or a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising a hydroxy functional group, a phenol functional group, or a carboxyl functional group; and a compound comprising both (meth)acrylate functionality and epoxy functionality.

11. The composition of claim 1, wherein the composition further comprises a polyhedral oligomeric silsesquioxane filler.

12. The composition of claim 1, wherein the filler composition further comprises fumed silica, colloidal silica, aluminosilicate glass, fluoroaluminosilicate glass, silica, quartz, strontium silicate, strontium borosilicate, lithium silicate, lithium alumina silicate, amorphous silica, ammoniated or deammoniated calcium phosphate, alumina, zirconia, tin oxide, titania, or a mixture comprising at least one of the foregoing fillers.

13. A method for the production of a dental restoration, comprising applying the composition of claim 1 to a site on a tooth to be restored; and curing the composition.

14. The method of claim 13, wherein the resin composition comprises an acrylate or methacrylate resin.

15. The method of claim 13, wherein the resin composition comprises polyurethane dimethacrylate, diurethane dimethacrylate, polycarbonate dimethacrylate, ethoxylated bisphenol A dimethacrylate, 2,2'-bis [4-(3-methacryloxy-2-hydroxy propoxy)-phenyl]-propane, or a mixture comprising at least one of the foregoing resins.

16. The method of claim 15, wherein the resin composition further comprises 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, butanedioldimethacrylate, dodecanedioldimethacrylate, 1,6-hexanedioldimethacrylate, or a mixture comprising at least one of the foregoing methacrylate monomers.

17. The method of claim 13, wherein the modified polyhedral oligomeric silsesquioxane filler comprises at least one functional group reactive with the resin composition.

18. The method of claim 17, wherein the reactive group comprises halide, alcohol, amine, isocyanate, acid, acid chloride, silanol, silane, acryl, methacryl, olefin, epoxy, or a mixture comprising at least one of the foregoing reactive groups.

19. The method of claim 17, wherein the reactive group comprises an acryl or methacryl.

20. The method of claim 17, wherein the reactive group comprises an alkoxysilane, a styrene, an olefin, an epoxy, a chlorosilane, an amine, an alcohol, a phenol, a phosphine, a norbornenyls, a nitrile, an isocyanate, a halide, an ester, or a mixture comprising at least one of the foregoing reactive groups.

21. The method of claim 13, wherein the modified polyhedral oligomeric silsesquioxane filler is the reaction product of
a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; D is SiO; Y is an organic group comprising an epoxy functional group; or
a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising an epoxy functional group; and
a (meth)acrylic acid, or a hydroxy (meth)acrylate of the formula

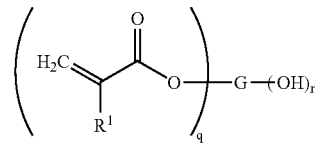

wherein q and r are independently integers from 1 to 6; G is a substituted or unsubstituted $C_1$–$C_{33}$ alkyl, substituted or unsubstituted aryl group, or ($C_1$–$C_6$) alkyl-oxy-($C_1$–$C_6$) alkyl; and $R^1$ is hydrogen or methyl, wherein the substitution is linear or branched, saturated or unsaturated $C_1$–$C_{12}$ alkyl; $C_1$–$C_{12}$ alkoxy; cyclic $C_3$–$C_7$ alkyl; halogens; ester groups; ether groups; amide groups; aryl; or a combination comprising at least one of the foregoing substitutions.

22. The method of claim 13, wherein the modified polyhedral oligomeric silsesquioxane filler is the reaction product of
a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; D is SiO; and Y is an organic group comprising a hydroxy functional group, a phenol functional group, or a carboxyl functional group; or
a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising a hydroxy functional group, a phenol functional group, or a carboxyl functional group; and
a compound comprising both (meth)acrylate functionality and epoxy functionality.

23. The method of claim 13, wherein the composition further comprises a polyhedral oligomeric silsesquioxane filler.

24. The method of claim 13, wherein the filler composition further comprises fumed silica, colloidal silica, aluminosilicate glass, fluoroaluminosilicate glass, silica, quartz, strontium silicate, strontium borosilicate, lithium silicate, lithium alumina silicate, amorphous silica, ammoniated or deammoniated calcium phosphate, alumina, zirconia, tin oxide, titania, or a mixture comprising at least one of the foregoing fillers.

25. A dental restoration, comprising the cured composition of claim 1.

26. The restoration of claim 25, wherein the resin composition comprises an acrylate or methacrylate resin.

27. The restoration of claim 25, wherein the resin composition comprises polyurethane dimethacrylate, diurethane dimethacrylate, polycarbonate dimethacrylate, ethoxylated bisphenol A dimethacrylate, 2,2'-bis [4-(3-methacryloxy-2-hydroxy propoxy)-phenyl]-propane, or a mixture comprising at least one of the foregoing resins.

28. The restoration of claim 27, wherein the resin composition further comprises 2-hydroxyethyl methacrylate, 2-hydroxypropyl methacrylate, ethylene glycol methacrylate, diethylene glycol methacrylate, tri(ethylene glycol)

dimethacrylate, tetra(ethylene glycol) dimethacrylate, butanedioldimethacrylate, dodecanedioldimethacrylate, 1,6-hexanedioldimethacrylate, or a mixture comprising at least one of the foregoing methacrylate monomers.

29. The restoration of claim 25, wherein the modified polyhedral oligomeric silsesquioxane filler is the reaction product of
a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; D is SiO; and Y is an organic group comprising an epoxy functional group; or
a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising an epoxy functional group; and
a (meth)acrylic acid, or a hydroxy (meth)acrylate of the formula

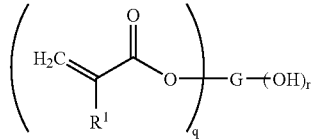

wherein q and r are independently integers from 1 to 6; G is a substituted or unsubstituted $C_1$–$C_{33}$ alkyl, substituted or unsubstituted aryl group, or ($C_1$–$C_6$) alkyl-oxy-($C_1$–$C_6$) alkyl; and $R^1$ is hydrogen or methyl, wherein the substitution is linear or branched, saturated or unsaturated $C_1$–$C_{12}$ alkyl; $C_1$–$C_{12}$ alkoxy; cyclic $C_3$–$C_7$ alkyl; halogens; ester groups; ether groups; amide groups; aryl; or a combination comprising at least one of the foregoing substitutions.

30. The restoration of claim 25, wherein the modified polyhedral oligomeric silsesquioxane filler is the reaction product of
a polyhedral oligomeric silsesquioxane monomer according to the formula $R_7T_4D_3(OY)_3$, wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; T is $SiO_{1.5}$; D is SiO; and Y is an organic group comprising a hydroxy functional group, a phenol functional group, or a carboxyl functional group; or
a polyhedral oligomeric silsesquioxane monomer according to the formula $R_{n-m}T_nY_m$ wherein R is $C_1$–$C_{24}$ straight, branched, or cyclic alkyl, $C_1$–$C_{24}$ aromatic, alkylaryl, or arylalkyl, wherein the alkyl or aromatic is optionally substituted with $C_1$–$C_6$ alkyl, halo, $C_1$–$C_6$ alkoxy, $C_1$–$C_6$ perhaloalkyl, or a combination comprising at least one of the foregoing substitutions; n is 6, 8, 10, or 12; m is 1 to n; T is $SiO_{1.5}$; and Y is an organic group comprising a hydroxy functional group, a phenol functional group, or a carboxyl functional group; and
a compound comprising both (meth)acrylate functionality and epoxy functionality.

* * * * *